US008515706B2

(12) United States Patent
Lee et al.

(10) Patent No.: US 8,515,706 B2
(45) Date of Patent: Aug. 20, 2013

(54) METHOD FOR CONTROLLING DRIVING OF TEST DEVICE AND ANALYTIC DEVICE FOR PERFORMING THE SAME

(75) Inventors: Jong Rip Lee, Bucheon-si (KR); Hyug Rae Cho, Seoul (KR); Seok Ho Kim, Bucheon-si (KR); Sung Hwa Lee, Anyang-Si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 434 days.

(21) Appl. No.: 12/858,123

(22) Filed: Aug. 17, 2010

(65) Prior Publication Data
US 2011/0046750 A1 Feb. 24, 2011

(30) Foreign Application Priority Data
Aug. 20, 2009 (KR) .......................... 10-2009-0077056

(51) Int. Cl.
G06F 19/00 (2006.01)
G06F 11/00 (2006.01)
G05B 11/00 (2006.01)

(52) U.S. Cl.
USPC .............................. 702/123; 700/12; 714/742

(58) Field of Classification Search
USPC ................ 702/123; 607/3; 700/12; 714/742
See application file for complete search history.

(56) References Cited

U.S. PATENT DOCUMENTS

| 2003/0078678 A1 | 4/2003 | Maturana et al. |
| 2006/0190794 A1* | 8/2006 | Murata ........................ 714/742 |
| 2009/0210019 A1* | 8/2009 | Kim et al. ....................... 607/3 |

OTHER PUBLICATIONS

European Search Report issued on Sep. 24, 2010 in counterpart European Patent Application No. 10170911.1.

* cited by examiner

Primary Examiner — Bryan Bui
(74) Attorney, Agent, or Firm — Sughrue Mion, PLC

(57) ABSTRACT

A method and apparatus for controlling driving of a test device that analyzes a sample are provided. The method includes identifying a test device, executing a script containing a plurality of operations to be performed to analyze the sample contained in the test device, wherein the script includes a plurality of operation commands, wherein at least one operation command among the plurality of operation commands includes a conditional statement, and wherein at least one operation command among the plurality of operation commands is designated to be executed according to whether the conditional statement is satisfied.

18 Claims, 5 Drawing Sheets

FIG. 3

| OPERATION NUMBER | CONDITIONAL STATEMENT | FIRST CONDITIONAL OPERATION NUMBER | SECOND CONDITIONAL OPERATION NUMBER | OPERATION NAME | OPERATION CONTENT | OPERATION NUMBER TO BE EXECUTED | NUMBER OF REPETITION TIMES |
|---|---|---|---|---|---|---|---|
| 10 | 11 | 12 | 13 | 14 | 15 | 16 | 17 |

FIG. 4

| OPERATION NUMBER | CONDITIONAL STATEMENT | FIRST CONDITIONAL OPERATION NUMBER | SECOND CONDITIONAL OPERATION NUMBER | OPERATION NAME | OPERATION CONTENT | OPERATION NUMBER TO BE EXECUTED | NUMBER OF REPETITION TIMES |
|---|---|---|---|---|---|---|---|
| #1 | | | | HOMOGENIZE BLOOD | ROTATION FOR 10 SECONDS AT 1800 RPM | | |
| #2 | | | | MEASURE AMOUNT OF BLOOD | LIGHT BEAM ILLUMINATED, MEASURE OPTICAL ABSORBANCE | | |
| #3 | INSUFFICIENT AMOUNT OF BLOOD | YES : #4 | NO : #5 | | | | |
| #4 | | | | ERROR WARNING | DISPLAY ERROR MESSAGE | | |
| #5 | | | | WAIT | 30 SECONDS | #1 | |
| #6 | | | | SERUM SEPARATION | ROTATION FOR 90 SECONDS AT 3600 RPM | | |
| #7 | | | | WAIT | 30 SECONDS | | |
| #8 | FIRST LASER FUNCTION ERROR ? | YES : #9 | NO : #10 | | | | |
| #9 | | | | VALVE MELTED | ILLUMINATE SECOND LASER BEAM ONTO VALVE POSITION FOR 5 SECONDS | #11 | |
| #10 | | | | VALVE MELTED | ILLUMINATE LASER BEAM ONTO VALVE POSITION FOR 5 SECONDS | | |
| #11 | VALVE INCOMPLETELY MELTED ? | YES : #10 | NO : #12 | | | | 3 |
| #12 | | | | WAIT | 30 SECONDS | | |
| #13 | | | | SERUM MOVED | ROTATION FOR 20 SECONDS AT 3600 RPM | | |
| #14 | | | | WAIT | 30 SECONDS | | |
| #15 | TEMPERATURE < 35℃ ? | YES : #16 | NO : #17 | | | | |
| #16 | | | | HEATING | HEATER OPERATED | #15 | 3 |
| #17 | TEMPERATURE < 40℃ ? | YES : #18 | NO : #19 | | | | |
| #18 | | | | COOLING | COOLER OPERATED | #15 | 3 |
| #19 | | | | MIXING | VIBRATION FOR 10 SECONDS AT 2400 RPM | | |
| #20 | INSUFFICIENT AMOUNT OF BLOOD IN CHAMBER INSUFFICIENT ? | YES : #21 | NO : #22 | | | | |
| #21 | | | | ERROR WARNING | DISPLAY ERROR MESSAGE | #13 | 3 |
| #22 | | | | ANALYZING | LIGHT BEAM ILLUMINATED IN CHAMBER, POSITION FOR 5 SECONDS | | |
| #23 | | | | DISPLAY RESULT | MEASURE OPTICAL ABSORBANCE | | |

METHOD FOR CONTROLLING DRIVING OF TEST DEVICE AND ANALYTIC DEVICE FOR PERFORMING THE SAME

CROSS-REFERENCE TO RELATED APPLICATION(S)

This application claims priority from Korean Patent Application No. 10-2009-0077056, filed on Aug. 20, 2009 in the Korean Intellectual Property Office, the entire disclosure of which is incorporated herein by reference.

BACKGROUND

1. Field

Apparatuses and methods consistent with exemplary embodiments relate to controlling a driving of a test device capable of testing a biochemical sample, and an analytic device for performing the same.

2. Description of the Related Art

In order to diagnose a disease in a patient, monitor the progress of disease, determine effects of medical treatment on the disease and determine a prognosis of the disease, a biological sample from the patient (e.g., blood or urine) is taken from the patient and subjected to testing and analysis.

In order to conveniently perform a variety of tests on a single sample at one time, a variety of sample test devices and a variety of analytic devices exist in the related art.

For example, in order to perform a biochemical test or an immune serum test on a patient's blood, a disc-type test device having a chamber which is pre-filled with a reagent used in such tests, has been developed. When a blood sample of a patient is introduced into the test device, and the test device is driven after being inserted into the analytic device, the blood sample flows into the chamber and reacts with the reagent. A result of the reaction is then analyzed by the analytic device using a spectroscopic analysis method.

Generally, if there is a error by tester (i.e., an operator of the test device), a faulty operation or other error occurs in the test device, the entire process is suspended and the test device must repeat the testing process again, starting from the initial step.

SUMMARY

Exemplary embodiments provide a method for controlling driving of a test device containing a sample.

Another exemplary embodiment provides a computer program product performing the method for driving the test device containing the sample, the computer program product being embodied on a computer readable medium and executed by a computer.

In accordance with an aspect of an exemplary embodiment, there is provided a method for an analytic device to control a driving of a test device containing a sample, the method including identifying a test device, and executing a script containing a plurality of operations to analyze the sample contained in the test device.

The script may include a plurality of operation commands, at least one operation command among the plurality of operation commands may include a conditional statement, and at least one operation command among the plurality of operation commands may be designated to be executed according to whether the conditional statement is satisfied.

The executing the script may include executing the designated operation command if it is determined that the conditional statement is satisfied when an operation corresponding to the operation command including the conditional statement is performed.

The at least one operation command among the plurality of operation commands may include information about a number of repeated retrial actions to be executed when an operation error occurs.

The performing of the script may include repeating an operation if an operation error occurs in the operation corresponding to the operation command including the information about the number of repeated retrial actions. The number of repeated retrial actions does not exceed a predetermined number of repeated retrial actions.

Each of the plurality of operation commands may be assigned a unique operation number. The analytic device sequentially performs operations corresponding to the corresponding operation command according to the order of the operation numbers when the script is executed. At least one operation command among the plurality of operation commands may include an operation command to be executed after a corresponding operation is completed. Therefore, the order of the operation numbers is not always limited thereto. If necessary, an operation corresponding to an operation command having a designated operation number may be executed after a corresponding operation command is performed.

In accordance with an aspect of another exemplary embodiment, there is provided a computer program product is provided for carrying out the above-described method, the computer program product embodied on a computer readable medium and executed by a computer to perform the method.

In accordance with an aspect of another exemplary embodiment, there is provided an apparatus for analyzing a sample contained in a test device, the apparatus including a recognition unit which identifies the test device, a driver which drives the test device, an analysis unit which analyzes the sample contained in the test device, and a controller which executes a script containing a plurality of operations to be performed to analyze the sample contained in the test device, and controls the recognition unit, the driver, and the analysis unit, wherein the script includes a plurality of operation commands, at least one operation command among the plurality of operation commands includes a conditional statement, and at least one operation command among the plurality of operations commands is designated to be executed according to whether the conditional statement is satisfied.

The controller may execute the designated operation command when it is determined that the conditional statement is satisfied when an operation corresponding to the operation command including the conditional statement is performed.

The controller may repeat performance of an operation if an operation error occurs in the operation including the information about a number of repeated retrial actions, where the number of repeated retrial actions does not exceed a predetermined number.

At least one operation command among the plurality of operation commands may include an operation command to be executed after a corresponding operation is completed.

BRIEF DESCRIPTION OF THE DRAWINGS

These and/or other aspects will become apparent and more readily appreciated from the following description of the exemplary embodiments, taken in conjunction with the accompanying drawings, of which:

FIG. 3 shows an architecture of operation commands constructing a script, according to an exemplary embodiment.

FIG. 4 shows an exemplary script including a plurality of operation commands, according to an exemplary embodiment.

DETAILED DESCRIPTION

Figure 1:
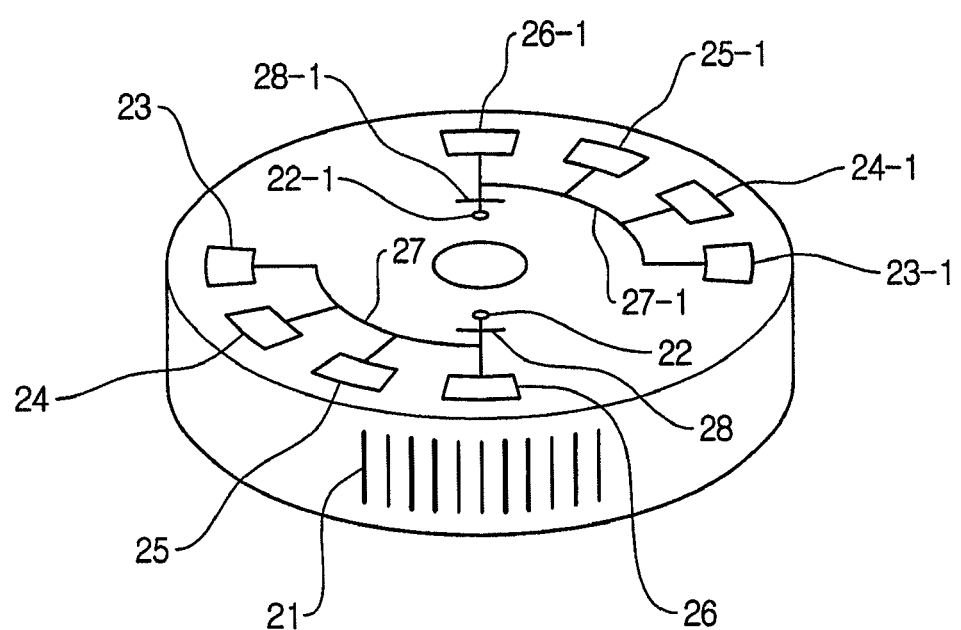
FIG. 1 illustrates an exemplary test device containing at least one reagent, as used in a method for controlling the driving of a test device, according to an exemplary embodiment.

Reference will now be made in detail to the exemplary embodiments, examples of which are illustrated in the accompanying drawings, wherein like reference numerals refer to like elements throughout. The following detailed description includes specific details in order to provide a thorough understanding of the exemplary embodiments. However, it will be apparent to those skilled in the art that the exemplary embodiments may be practiced without such specific details.

FIG. 1 illustrates an exemplary test device containing at least one reagent, which may be used in a method for controlling the driving of a test device, according to an exemplary embodiment. The test device shown in FIG. 1 is a disc-shaped device capable of being rotated by a centrifugal force.

The test device includes a plurality of chambers 23, 24, 25, 26, 23-1, 24-1, 25-1 and 26-1 containing different reaction reagents therein, channels 27 and 27-1 which provide paths along which a fluid flows, and valves 28 and 28-1 that open and close to control the flow of fluid to the channels 27 and 27-1. These finely-flowing structures may be symmetrically arranged on the disc-shaped test device, as illustrated in FIG. 1.

In this exemplary embodiment, the valves 28 and 28-1 are normally-closed valves including a phase-transition material that initially is in a solid state to close a channel thereby blocking the flow of a fluid and melts when irradiated with electromagnetic energy to open the channel. However, this is merely an example, and the valves 28 and 28-1 may be capillary valves that are passively opened when a pressure exceeding a predetermined value is applied, or a valves actively operating by receiving external power or energy according to an operating signal.

In one exemplary embodiment, a disc identifier (ID) consisting of a barcode 21 may be provided on a circumferential surface of the test device. An analytic device (not shown) reads the barcode 21, and inquires with a pre-constructed database to determine which kind of tests can be performed by the test device, or which kind of reagent is contained in each chamber 23, 24, 25, 26, 23-1, 24-1, 25-1 or 26-1. In addition, the analytic device calls a script for driving the test device. The script will be described later.

In order to analyze a sample, a tester supplies a sample (e.g., a biochemical sample such as blood or urine) to be analyzed into the test device via an inlet 22, and inserts the test device including the sample into the analytic device.

The analytic device analyzes the sample by driving the inserted test device. In one non-limiting example, the analytic device applies a laser to the location of a phase transition valve 28 of a channel located between the inlet 22 and the chambers 23, 24, 25 and 26, such that the valve 28 is melted. Thereafter, the analytic device generates a centrifugal force by rotating the test device, which transfers the sample to the chambers 23, 24, 25 and 26 by the centrifugal force. The sample reacts with the reagent within each chamber 23, 24, 25 or 26. The analytic device illuminates a light on the location of each chamber 23, 24, 25, or 26, and analyzes optical absorbance or optical transmittance of the reaction result, such that the analytic device qualitatively or quantitatively analyzes the sample.

Figure 2:
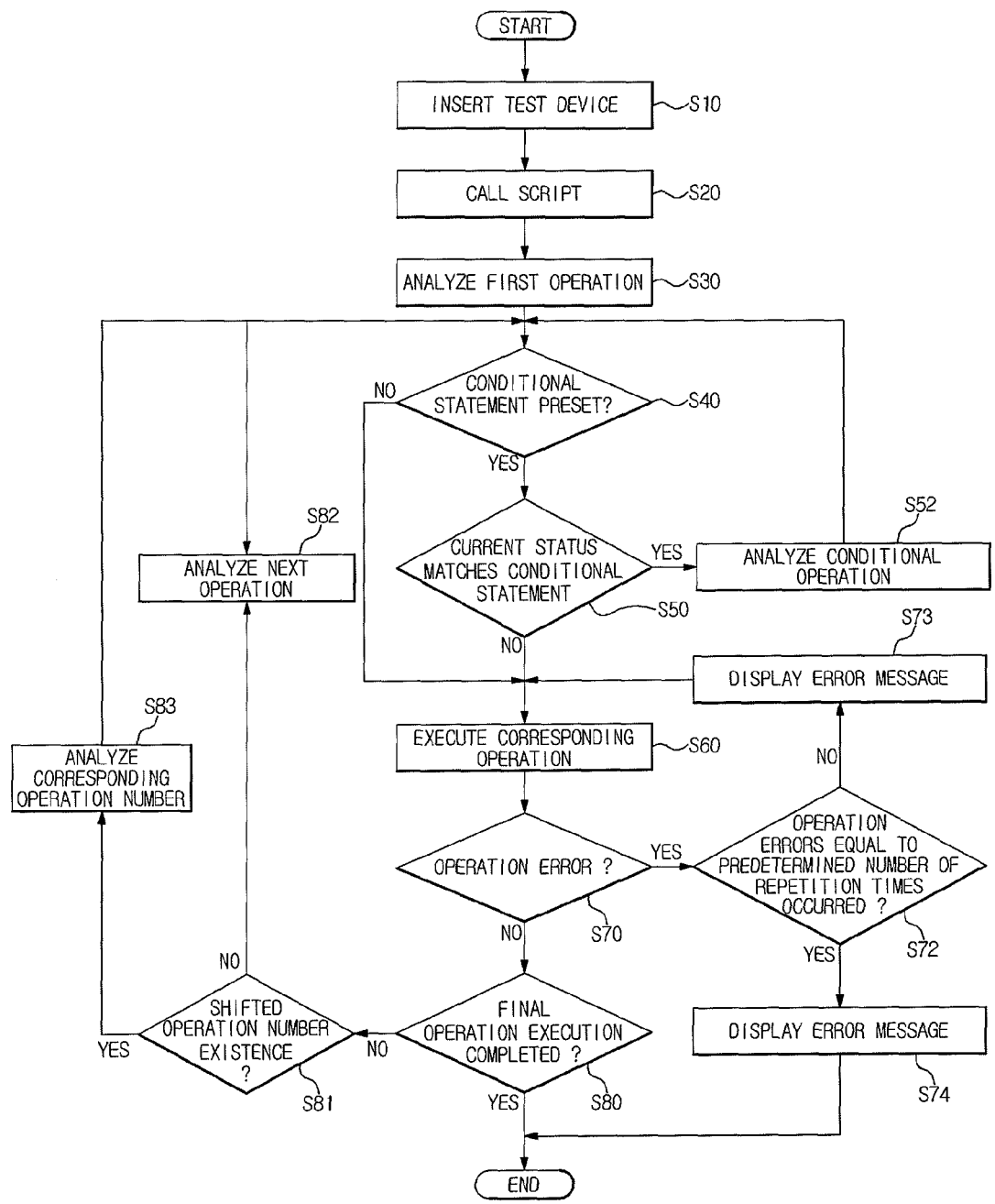
FIG. 2 is a flowchart illustrating a method for controlling the driving of a test device when an analytic device analyzes a sample inserted into the test device, according to an exemplary embodiment.

FIG. 2 is a flowchart illustrating a method for controlling the driving of a test device when an analytic device analyzes a sample inserted into the test device, according to an exemplary embodiment. In accordance with the control method shown in FIG. 2, the analytic device may appropriately drive the test device in response to an operation error or a variation in environmental conditions.

A method for controlling the driving of the test device in accordance with one exemplary embodiment will hereinafter be described with reference to FIG. 2.

Referring to FIG. 2, when the test device is inserted into the analytic device at operation S10, the analytic device recognizes the test device, and accesses to a database for information on the test device, such that it calls a script corresponding to the test device at operation S20. Although this particular exemplary embodiment discloses that the script is stored in a database contained in or communicably linked to the analytic device, it should noted that the script may also be stored in another terminal connected to the analytic device over a network.

In one exemplary embodiment, the script is a set of commands (or command statements) in which a series of operations for analyzing the sample is defined, and is composed of a plurality of operation commands.

FIG. 3 shows an architecture of operation commands constructing the script, according to an exemplary embodiment. The operation commands may include an operation number 10, a conditional statement 11, operation numbers (i.e., a first conditional operation number 12 and a second conditional operation number 13) to be carried out when a statement is determined to be the conditional statement, an operation name 14, operation content 15, an operation number 16 to be executed after the completion of operation, information about the number of repeated retrial actions 17 to be executed in case of an operation error, and the like.

FIG. 4 illustrates an exemplary script including a plurality of operation commands, according to an exemplary embodiment. The script shown in FIG. 4 includes a plurality of operation commands for carrying out a series of operations used for analyzing the sample, such as a blood sample, in the test device.

In one exemplary embodiment, the analytic device analyzes a first command 40 (i.e., an operation command having an operation number #1) at operation S30, and determines the presence or absence of a conditional statement 11 in the command at operation S40. Since there is no conditional statement 11 in the first command 40, the analytic device rotates the test device for 10 seconds at a speed of 1800 revolutions per minute (rpm) so as to homogenize the blood inserted into the test device, according to the command, or operation name 14, at operation S60. The operation content 15 of the first command 40 and designated variables (i.e., rotation speed, rotation direction, rotation time, etc.) may be written in computer-recognizable languages such as Extensible Markup Language (XML). The test device is driven according to the operation content 15.

Thereafter, at operation S80, the last command of the script has not been carried out yet, such that the next operation command (i.e., the second command 41) is analyzed at operation S82. After the next operation name 14 is analyzed, the amount of blood is measured in response to the operation name 14 of the second command 41 at operation S60.

A next operation command (i.e., a third command 42) is analyzed at operation S82. Since there is a conditional statement 11 in the third command 42 at operation S40, the conditional statement is evaluated. It is therefore determined whether the amount of blood inserted into the test device is sufficient, i.e. whether there is less than a predetermined minimum amount of blood in the test device, at operation S50.

If it is determined that the amount of blood inserted into the test device is insufficient, a first conditional operation number 12 satisfying the condition (i.e., indicating that a fourth command 43 be executed) is analyzed at operation S52, and an error message indicating a deficiency of blood is displayed according to the operation content 15 of the fourth command 43 at operation S60. Thereafter, if the tester inserts an additional amount of blood into the test device, the current process is shifted back to a first command 40 indicating the designated operation command, and the first command 40 is analyzed at operation S83. This results when an operation command of the fourth operation 43 executes the operation number 16 (i.e., an operation number 16 to be executed) to be carried out after the completion of the fourth command 43, as designated at operation S81. The operation number to be executed is the first operation, so the first operation 40 is re-performed.

If, during execution of the third command 42, it is determined that there is a sufficient amount of blood inserted into the test device at operation S50, a second conditional operation number 13 (i.e., indicating that a fifth command 44 be executed) satisfying the above-mentioned condition is analyzed at operation S52, and a waiting time of 30 seconds is held according to the operation content 15 of the fifth command 44, at operation S60.

Thereafter, a next operation command, i.e., a sixth command 45, is analyzed at operation S82. In order to separate serum of the blood according to the operation content 15 of the sixth command 45, the test device is rotated for 90 seconds at 3600 rpm, at operation S60.

A next operation command, i.e., a seventh command 46, is analyzed at operation S82, and a waiting time of 30 seconds is held according to the operation content 15 of the seventh command 46 at operation S60.

A next operation command, i.e., an eighth command 47, is analyzed at operation S82. Since there is a conditional statement 11 in the eighth command 47 at operation S40, the conditional statement is evaluated and it is determined whether a faulty operation has occurred in the functions of several laser sources, at operation S50.

If it is determined that the faulty operation has occurred in any one of the laser sources, a first conditional operation number 12 (i.e., providing for execution of a ninth command 48) satisfying the above condition is analyzed at operation S52. A laser beam is illuminated on a valve using only the remaining normal laser sources, according to the operation content 15 of the ninth command 48, so that a valve is melted, at operation S60. Thereafter, the operation command (i.e., an operation number to be executed 16) to be carried out after the completion of the ninth command 48 is designated at operation S81, such that a current process is shifted to an eleventh command 50 indicating the designated operation command, at operation S83.

If all the current laser sources are normal at operation S50, a second conditional operation number 13 (i.e., providing for execution of a tenth command 49) satisfying the above condition is analyzed at operation S52, and respective valves are melted by respective laser beams according to the operation content 15 of the tenth command 49 at operation S60.

A next operation command, i.e., an eleventh command 50, is analyzed at operation S82. It is determined whether respective valves have been completely or incompletely melted according to the content of a conditional statement 11 of the above eleventh command 50 at operation S50.

If the valve is incompletely melted, a process follows the first conditional operation number 12 (i.e., providing for execution of the tenth command 49) satisfying the above condition at operation S52, and the valve melting operation is re-executed at operation S60. Thereafter, if the valve is incompletely melted although the valve melting operation has been executed at operation S70, a predetermined number of valve melting operations is reattempted within the limit of the number of repetition times 17 (i.e., three times) written in the tenth command 49 at operation S72, and an error message is then displayed at operation S73. In this way, if the valve is not completely melted after the valve melting operation has been repeated three times at operation S73, an error message indicating that the analyzing operation cannot be executed is displayed at operation S74, and the analyzing operation is then terminated.

If the valve is completely melted, a current process is shifted to a second conditional operation number 13 (i.e., providing for execution of the twelfth command 51) satisfying the above condition at operation S52, and a waiting time of 30 seconds is held according to the operation content 15 of the $12^{th}$ command 51 at operation S60.

A next operation command (i.e. a thirteenth command 52) is analyzed at operation S82, and the test device is rotated for 20 seconds at 3600 rpm so as to move a blood serum to chambers 23, 24, 25, and 26 (See FIG. 1), each of the chambers including a reagent according to the operation content 15 of the thirteenth command 52 at operation S60.

A next operation command (i.e., a fourteenth command 53) is analyzed at operation S82, and a waiting time of 30 seconds is held according to the operation content 15 of the fourteenth command 53, at operation S60.

A next operation command (i.e., a fifteenth command 54) is analyzed at operation S82, and a current temperature is measured in response to a content of a conditional statement 11 of the command at operation S50, so that it can be determined whether a reaction temperature between the blood and the reagent is in the range from 35 degrees Celsius (° C.) to 40° C., i.e., very close to body temperature. If the temperature is less than 35° C., a current process is shifted to a first conditional operation number 12 (i.e., providing for execution of a sixteenth command 55) satisfying the above condition at operation S52, and a heater is operated at operation S60. If the temperature is less than 35° C. even though the heater has been operated, the above-mentioned operations are reattempted within the limit of the number of repetition times 17 (i.e., three times) at operation S72.

If the temperature is higher than 40° C., a current process is shifted to a second conditional operation number 13 (i.e., providing for execution of an eighteenth command 57) satisfying the above condition at operation S52, and a cooler is operated at operation S60. If the temperature is higher than 40° C. even though the cooler has been operated, the above-mentioned operations are reattempted within the limit of the number of repetition times 17 (i.e., three times) at operation S72.

A next operation command, i.e., a nineteenth command 58, is analyzed at operation S82, and a mixing operation 14 is carried out, where the test device is vibrated for 10 seconds at 2400 rpm such that a blood serum reacts with a reagent contained in each chamber 23, 24, 25 or 26 (See FIG. 1) at operation S60.

Thereafter, a next operation command, i.e., a twentieth command 59, is analyzed at operation S82. Since the twentieth command includes a conditional statement 11 at operation S40, a current process is shifted to the inside of the current chamber, such that the conditional statement is evaluated and it is determined whether the amount of blood having reacted with the reagent is less than a predetermined minimum amount of blood at operation S50.

If it is determined that the amount of blood present in a current chamber is insufficient, a first conditional operation number 12 (i.e., providing for execution of a twenty-first command 60) satisfying the above condition is analyzed at operation S52, and an error message indicating the insufficient amount of blood is displayed according to an operation content 15 of the twenty-first command 60 at operation S60. Thereafter, a current process is shifted to the thirteenth command, so that a serum-moving operation for moving the blood serum to the chamber is reattempted within the limit of the number of repetition times 17 (i.e., three times) at operation S72.

If it is determined that the amount of blood present in the chamber is sufficient, a second condition operation number 13 (i.e., providing for the execution of a twenty-second command 61) satisfying the above condition is analyzed at operation S52, and a light beam is illuminated into the chamber according to an operation content 15 of the twenty-second command, so as to inspect optical absorbance or optical transmittance. Based on the analysis of the optical absorbance or transmittance, the density of a component (e.g., an antibody component reacting with a specific antigen) contained in the blood and reacting with a specific reagent is analyzed at operation S60.

Thereafter, a next operation command, i.e., the twenty-third command 62, is analyzed at operation S82, wherein the optical absorbance is measured according to operation content 15, and the analyzed result is displayed on a screen according to the operation name 16, at operation S60. The twenty-third command 62 is the last operation command of the script at operation S80, so that the test device halts operation after the above operation command 62 has been performed.

In accordance with the above-mentioned method for controlling the driving of the test device, if an error occurs while the test device is analyzing the blood sample, the test device does not return to the initial step after terminating all processes, but returns to a previous step for recovering the error so that the operations are re-executed. Therefore, there is no need to repeat the previously-executed procedures. In the case where the analytic device analyzes the test device, the analytic device can variably control the test device in response to a current condition. In addition, the exemplary embodiment is able to provide a processing method to be executed in case of a control failure.

Although the script used in the exemplary embodiment includes a general operation command, an operation command including a conditional statement, an operation command in which an operation number to be executed after the completion of an operation is designated, and an operation command in which the number of repetition times in case of an error is designated, the above-mentioned script is disclosed only for illustrative purposes of the various exemplary embodiments. Therefore, it will be appreciated by those skilled in the art that in additional exemplary embodiments, only a general operation command and an operation command including a conditional statement can be used in the aforementioned script.

In accordance with an exemplary embodiment, a command including the conditional statement may include two conditional commands, i.e., a first conditional command to be executed when the command matches the conditional statement, and a second conditional command to be executed when the command does not match the conditional statement. However, the command may be divided into three or more commands according to conditions as necessary. In addition, the command may be branched into other commands only when the command corresponds to a condition. If the command does not correspond to a condition, an operation assigned to a command may be carried out without any change.

According to one exemplary embodiment, although a reaction environment such as a temperature is checked at a specific step, the reaction environment may be checked in all steps performed while the test device is being driven.

Figure 5:
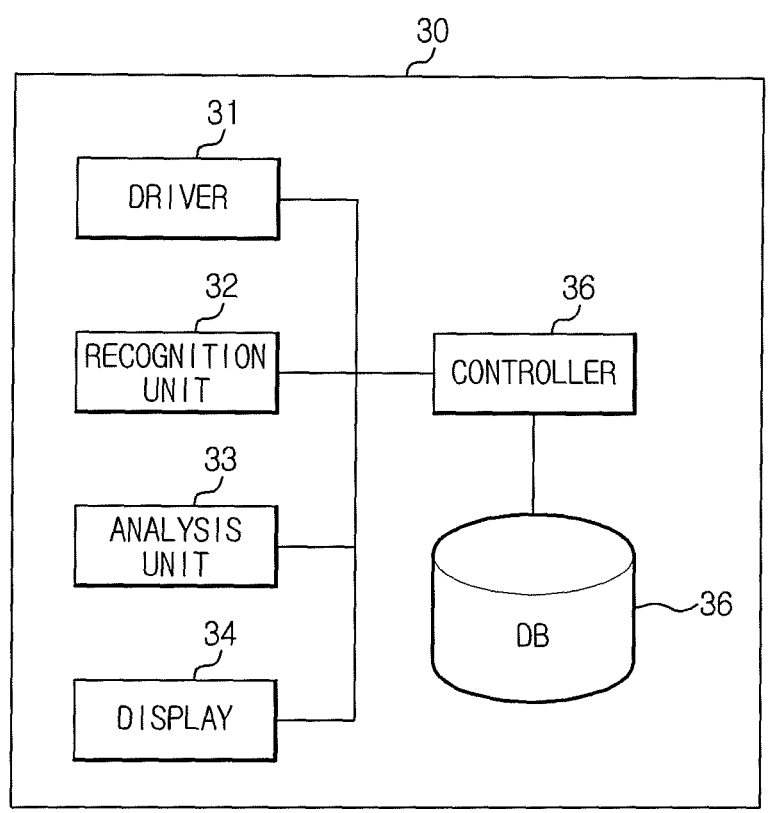
FIG. 5 is a block diagram illustrating an analytic device for controlling the driving of a test device, according to another exemplary embodiment.

FIG. 5 is a block diagram illustrating an analytic device for controlling the driving of a test device, according to another exemplary embodiment.

Referring to FIG. 5, the analytic device 30 includes a test device recognition unit 32, a database (DB) 35, a driver 31, an analysis unit 33, a display 34, and a controller 36. When the test device is inserted into the analytic device 30, the test device recognition unit 32 recognizes the test device, for example by recognizing an ID of the test device. The database (DB) 35 stores information about a script for each test device ID, including information about available test items, or information about categories of included reagents. The driver 31 rotates the test device or drives the test device in a manner such that a light source is illuminated onto the test device. The analysis unit 33 analyzes an optical signal characteristic such as optical absorbance or optical transmittance with respect to the light source illuminated onto the sample and reagent, so as to qualitatively or quantitatively analyze the sample. The display 34 displays the analyzed result. The controller 36 controls operations of the above-mentioned components. The controller 36 calls a script for defining each operation to be performed to analyze the sample contained in the test device, and controls the recognition unit 32, the driver 31, or the analysis unit 33 in response to the called script.

When the test device is driven in response to an operation command including a conditional statement, the controller 36 determines whether a current status of the test device matches the above conditional statement, such that it performs the designated operation command according to the determined result.

If an error occurs in an operation corresponding to the operation command including information of the number of repeated retrial actions to be executed in case of an operation error, the controller 36 reattempts execution of the operation while simultaneously controlling the number of operations not to exceed the above number of repeated retrial actions.

When an operation command to be executed after the completion of a previous operation is additionally designated, the controller 36 executes the designated operation command after the completion of the previous operation, such that it performs an operation corresponding to the designated operation command.

Although a few exemplary embodiments have been shown and described, it will be appreciated by those skilled in the art that changes may be made in these embodiments without departing from the principles and spirit of the inventive concept, the scope of which is defined in the claims and their equivalents.

What is claimed is:

1. A method for controlling driving of a test device containing a sample, the method comprising:
   identifying a test device; and
   executing a script containing a plurality of operations to be performed to analyze the sample contained in the test device, wherein the script comprises a plurality of operation commands,
   wherein at least one operation command among the plurality of operation commands includes a conditional statement, and
   wherein at least one operation command among the plurality of operation commands is designated to be executed according to whether the conditional statement is satisfied.

2. The method according to claim 1, wherein the executing the script comprises:
   executing the designated operation command when it is determined that the conditional statement is satisfied when an operation corresponding to the operation command including the conditional statement is performed.

3. The method according to claim 1, wherein each of the plurality of operation commands is assigned a unique operation number.

4. The method according to claim 1, wherein at least one operation command among the plurality of operation commands includes information about a number of repeated retrial actions to be executed when an operation error occurs.

5. The method according to claim 4, wherein the executing the script comprises:
   repeating performance of an operation if the operation error occurs in the operation corresponding to the operation command including the information about the number of repeated retrial actions, wherein the number of repeated retrial actions does not exceed a predetermined number.

6. The method according to claim 5, further comprising:
   displaying an error message when the operation error occurs even though operation errors equal to the number of repeated retrial actions have been performed.

7. The method according to claim 1, wherein at least one operation command among the plurality of operation commands includes an operation command to be executed after a corresponding operation is completed.

8. The method according to claim 7, wherein the executing the script comprises:
   performing the corresponding operation corresponding to the operation command including the operation command to be executed after the corresponding operation is completed; and
   after completing the corresponding operation, executing the operation command to be executed after the corresponding operation is completed.

9. A method for controlling driving of a test device containing a sample, the method comprising:
   identifying a test device;
   executing a script containing a series of operations to be performed to analyze the sample,
   wherein the script includes a plurality of operation commands,
   wherein at least one operation command includes information about a number of repeated retrial actions to be executed in case of an operation error, and
   wherein the executing the script comprises repeating an operation if an operation error occurs in the operation corresponding to the operation command including information about the number of repeated retrial actions, where the number of repeated retrial actions is not greater than a predetermined number of repeated retrial actions.

10. A method for controlling driving of a test device containing a sample, the method comprising:
    identifying a test device;
    executing a script containing a plurality of operations to be performed to analyze the sample, wherein the script includes a plurality of operation commands, wherein at least one operation command among the plurality of operation commands includes a designated operation command to be executed after a corresponding operation is completed, and
    wherein the executing the script comprises, after completing the corresponding operation corresponding to the operation command including the designated operation command to be executed after the corresponding operation is completed, executing the designated operation command.

11. A computer program product controlling a driving of a test device containing a sample, the computer program product embodied on a computer readable medium and when executed by a computer, performing the method of claim 1.

12. An apparatus for analyzing a sample contained in a test device, the apparatus comprising:
    a recognition unit which identifies the test device;
    a driver which drives the test device;
    an analysis unit which analyzes the sample contained in the test device; and
    a controller which executes a script containing a plurality of operations to be performed to analyze the sample contained in the test device, and controls the recognition unit, the driver, and the analysis unit according to the executed script, wherein the script includes a plurality of operation commands, wherein at least one operation command among the plurality of operation commands includes a conditional statement and
    wherein at least one operation command among the plurality of operations commands is designated to be executed according to whether the conditional statement is satisfied.

13. The apparatus according to claim 12, wherein the controller executes the designated operation command when it is determined that the conditional statement is satisfied when an operation corresponding to the operation command including the conditional statement is performed.

14. The apparatus according to claim 12, wherein each of the plurality of operation commands is assigned a unique operation number.

15. The apparatus according to claim 12, wherein at least one operation command among the plurality of operation commands includes information about a number of repeated retrial actions to be performed when an operation error occurs.

16. The apparatus according to claim 15, wherein the controller repeats performance of an operation if the operation error occurs in the operation including the information about the number of repeated retrial actions, wherein the number of repeated retrial actions does not exceed a predetermined number.

17. The apparatus according to claim 12, wherein at least one operation command among the plurality of operation commands includes an operation command to be executed after a corresponding operation is completed.

18. The apparatus according to claim 17, wherein the controller, after completing the corresponding operation corresponding to the operation command including the operation command to be executed after the corresponding operation is completed, executes the operation command to be executed after the corresponding operation is completed.

* * * * *